(12) United States Patent
Guo et al.

(10) Patent No.: US 10,327,699 B2
(45) Date of Patent: Jun. 25, 2019

(54) BODY FAT MEASURING APPARATUS, SYSTEM AND PAIRING METHOD THEREOF

(71) Applicants: INVENTEC APPLIANCES (PUDONG) CORPORATION, Shanghai (CN); INVENTEC APPLIANCES CORP., New Taipei (TW); INVENTEC APPLIANCES (NANCHANG) CORPORATION, High-Tech Zone of Nanchang, Jiangxi (CN)

(72) Inventors: Houjin Guo, Jiangxi (CN); Xiaolong Xu, Jiangxi (CN); Ying Hu, Jiangxi (CN)

(73) Assignees: Inventec Appliances (Pudong) Corporation, Shanghai (CN); Inventec Appliances Corp., New Taipei (TW); Inventec Appliances (Nanchang) Corporation, Jiangxi (CN)

( * ) Notice: Subject to any disclaimer, the term of this patent is extended or adjusted under 35 U.S.C. 154(b) by 310 days.

(21) Appl. No.: 15/171,436

(22) Filed: Jun. 2, 2016

(65) Prior Publication Data

US 2017/0238869 A1 Aug. 24, 2017

(30) Foreign Application Priority Data

Feb. 23, 2016 (CN) .......................... 2016 1 0100143

(51) Int. Cl.
*A61B 5/00* (2006.01)
*A61B 5/053* (2006.01)
(Continued)

(52) U.S. Cl.
CPC .......... *A61B 5/4872* (2013.01); *A61B 5/0004* (2013.01); *A61B 5/0538* (2013.01);
(Continued)

(58) Field of Classification Search
CPC ..... A61B 5/0004; A61B 5/053; A61B 5/0531; A61B 5/0537; A61B 5/0538; A61B 5/4872
See application file for complete search history.

(56) References Cited

U.S. PATENT DOCUMENTS 7,932,472 B2 * 4/2011 Oseko ................. A61B 5/0537
128/921
9,408,553 B2 * 8/2016 Hamaguchi .......... A61B 5/0537
(Continued)

FOREIGN PATENT DOCUMENTS

TW  I489973 B  7/2015

*Primary Examiner* — Max F Hindenburg
(74) *Attorney, Agent, or Firm* — Muncy, Geissler, Olds & Lowe, P.C.

(57) ABSTRACT

A body fat measuring apparatus, system and pairing method thereof are provided. The body fat measuring apparatus and system include: a measuring unit provided for determining a current body weight and a current impedance of a user, and the current body weight and the current impedance used as a current analysis data set; a storage unit provided for cumulatively storing a user name, a user characteristic information related to the user name, and a plurality of recorded analysis data sets corresponding to the user names; and a processor provided for pairing the user name, reading the user characteristic information related to the user name, and obtaining a body fat information by calculating with the current body weight and the current impedance of the user.

13 Claims, 3 Drawing Sheets

(51) Int. Cl.
*G01G 19/44* (2006.01)
*G01G 19/50* (2006.01)

(52) U.S. Cl.
CPC .......... *A61B 5/4509* (2013.01); *A61B 5/4875* (2013.01); *A61B 5/7225* (2013.01); *G01G 19/44* (2013.01); *G01G 19/50* (2013.01); *A61B 2560/0468* (2013.01); *A61B 2560/0475* (2013.01)

(56) References Cited

U.S. PATENT DOCUMENTS

| | | | | |
|---|---|---|---|---|
| 9,474,934 B1* | 10/2016 | Krueger | ............... | G09B 19/003 |
| 9,498,137 B2* | 11/2016 | Kovacs | ................ | A61B 5/0205 |
| 9,980,663 B2* | 5/2018 | Wabel | .................. | A61B 5/0537 |
| 10,028,673 B2* | 7/2018 | Kumagai | ............. | A61B 5/0537 |

\* cited by examiner

BODY FAT MEASURING APPARATUS, SYSTEM AND PAIRING METHOD THEREOF

CROSS REFERENCE TO RELATED APPLICATION

The present application is based on, and claims priority from, China (International) Application Serial Number 201610100143.9, filed Feb. 23, 2016, the invention of which is hereby incorporated by reference herein in its entirety.

FIELD OF THE INVENTION

The present invention relates to body fat measurement field, particularly relates to a body fat measuring apparatus, system and pairing method thereof that adopts KNN algorithm process for pairing a user name with a user.

BACKGROUND OF THE INVENTION

With increasing knowledge on enhancement of living quality and health, modern people that have heavy works and tight life steps prefer health to business success. Thus, there are many leisure activities growing, such as bicycle riding or marathon racing.

On one hand, people have been keeping their own good shapes by engaging outdoor leisure activities. On the other hand, household or portable measurement apparatus are more and more popular and people know body condition themselves with such the measurement apparatus, as well as adjust both frequency and strength of outdoor leisure exercise and control diet. For example, weight meter for weight measurement and body fat meter for body fat measurement are popular in markets. Present body fat meter calculates out body percentage of user by detecting impedance changing of user body with a sensor that senses current passing through the user body and combining the impedance changing and current body weight of the user body under consideration of user characteristic information such as height, gender or age, inputted by the user.

It is inconvenient and troublesome for a user to repeatedly input his/her characteristic information such as height, gender or age during measurement of body fat. For example, Taiwan Patent No. I489973 discloses a portable body fat measuring apparatus whose central control unit reminds the user of inputting user parameters such as weight, height, age, or gender after measurement completion, and the portable body fat measuring apparatus calculates out fat ratio of the user according to the user parameters. Moreover, another prior technology identifies the user by matching a current body weight W and current impedance Z with single recorded weight Wm and single recorded impedance Zm. An algorithm process used in the another prior technology is following:

$$Ad = |W - Wm| * \alpha + |Z - Zm| * \beta$$

However, it often makes mistakes during the pairing of the user name and the user by using the prior technology because there is only single record of recorded weight Wm and recorded impedance Zm to be remained in body fat measuring meter.

Accordingly, it is one technical issue of the present invention to resolve inconveniences of repeatedly inputting user name and user characteristic information and improvements on accuracy pairing of a user name and a user.

SUMMARY OF THE INVENTION

A body fat measuring apparatus is provided herein, which includes: a measuring unit provided for determining a current body weight and a current impedance of a user, and the current body weight and the current impedance used as a current analysis data set; a storage unit provided for cumulatively storing a user name, a user characteristic information related to the user name, and a plurality of recorded analysis data sets corresponding to the user names; and a processor provided for pairing the user name, reading the user characteristic information related to the user name, and obtaining a body fat information by calculating with the current body weight and the current impedance of the user; wherein the processor reads the current body weight, the current impedance and the plurality of recorded analysis data sets to perform an algorithm process to obtain a plurality of distances; sorts the plurality of distances sequentially from the minimum value to the maximum value; selects the K (K is 1-10) values out of the plurality of distances upwardly from the minimum value of the sorting result; groups the K (K is 1-10) values out of the plurality of distances separately according to the user names related to the plurality of recorded analysis data sets to form at least one group; performs a grouping operation on each of the at least one group and taking the maximum result from the at least one group; pairs the user with the user name related to the at least one group with the maximum result; and stores the current analysis data set in the plurality of recorded analysis data sets of the storage unit corresponding the user names.

In one preferred example, the body fat measuring apparatus further includes a wireless transmission unit which wirelessly connects a portable electronic device with the body fat measuring apparatus, wherein the user can create the user name and the user characteristic information related to the user name in the storage unit via the portable electronic device, or the body fat information is transferred to the portable electronic device via the wireless transmission unit.

In one preferred example, the portable electronic device is a laptop, a tablet, a personal digital assistant, a mobile phone, a watch, or a game console.

In one preferred example, the body fat measuring apparatus further includes a display unit, wherein displaying information of the display unit includes the current body weight, the user name, and the user characteristic information that is related to the user name, or the body fat information.

In one preferred example, a calculation formula of the algorithm process is $$Dn = |W - Wm| * \alpha + |Z - Zm| * \beta,$$

wherein W is the current body weight, Z is the current impedance, Wm is one recorded body weight of the plurality of recorded analysis data sets, Zm is one recorded impedance of the plurality of recorded analysis data sets, and β is the recorded analysis data sets correspond to their own user names.

In one preferred example, when the units of the current body weight and the recorded body weight are kilograms, the range of α value is from 0.2~0.5; when the units of the current body weight and the recorded body weight are grams, the range of α value is from 200~500; and when the units of the current impedance and the recorded impedance are ohms, the range of β value is from 1~5.

Accordingly, a body fat measuring system composed of a portable electronic device and a body fat measuring device, wherein the body fat measuring device includes: a wireless transmission unit, a measuring unit, a storage unit, and a processor, wherein the measuring unit determines a current body weight and a current impedance of a user as a current analysis data set; the storage unit stores a user name, a user characteristic information related to the user name, and a plurality of recorded analysis data sets corresponding the user names cumulatively; the processor reads the current body weight, the current impedance and the plurality of recorded analysis data sets to perform an algorithm process to obtain a plurality of distances, then the plurality of distances are sorted sequentially from a minimum value to a maximum value; the processor selects the K (K is 1-10) values out of the plurality of distances upwardly from the minimum value of the sorting result and the K values (K is 1-10) out of the plurality distances is then performed a grouping operation according to the user names related to the plurality of recorded analysis data sets, and the maximum result of the grouping operation is taken out, in which the user name of the maximum result is paired with the user, a body fat information is obtained by calculating with the current analysis data set and the user characteristic information related to the user name which is paired with the user, and then the current analysis data set is stored in the plurality of recorded analysis data sets of the storage unit corresponding to the user name; and a portable electronic device which is wirelessly connected with the wireless transmission unit, transfers the user name and the user characteristic information related to the user name to the body fat measuring device, or receives the body fat information via the wireless transmission unit.

In one preferred example, body fat measuring device further includes a display unit and displaying information of the display unit including the current body weight, the user name, the user characteristic information related to the user name, or the body fat information.

Accordingly, A body fat measuring method includes: (a) measuring a user to obtain a current body weight and a current impedance of the user, and treating the current body weight and the current impedance as a current analysis data set; (b) performing an algorithm process with the current body weight, the current impedance and a plurality of recorded analysis data sets corresponding to the user names to obtain a plurality of distances; (c) sorting the plurality of distances sequentially from the minimum value to the maximum value, selecting the K (K is 1-10) values out of the plurality of distances upwardly from the minimum value of the sorting result; (d) performing a grouping operation with the K (K is 1-10) values out of the plurality of distances according to the user names related to the plurality of recorded analysis data sets, and the maximum result of the grouping operation is taken out and the user name of the maximum result is paired with the user; (e) reading a user characteristic information related to the user name which is paired with the user, and obtaining a body fat information by calculating with the current body weight, the current impedance, and the user characteristic information; and (f) storing the current analysis data set in the plurality of recorded analysis data sets corresponding the user names.

In one preferred example, the plurality of recorded analysis data sets in step (b) includes a recorded body weight, a recorded impedance, and a calculation formula of the algorithm process is $$Dn=|W-Wm|*\alpha+|Z-Zm|*\beta,$$

wherein W is the current body weight, Z is the current impedance, Wm is one recorded body weight of the plurality of recorded analysis data sets, Zm is one recorded impedance of the plurality of recorded analysis data sets, and β is the recorded analysis data sets correspond to their own user names, respectively; when the units of the current body weight and the recorded body weight is kilograms, the range of α value is from 0.2~0.5; when the units of the current body weight and the recorded body weight are grams, the range of α value is from 200~500; and when the units of the current impedance and the recorded impedance is ohms, the range of β value is from 1~5.

DETAILED DESCRIPTION OF THE PREFERRED EMBODIMENT

Figure 1:
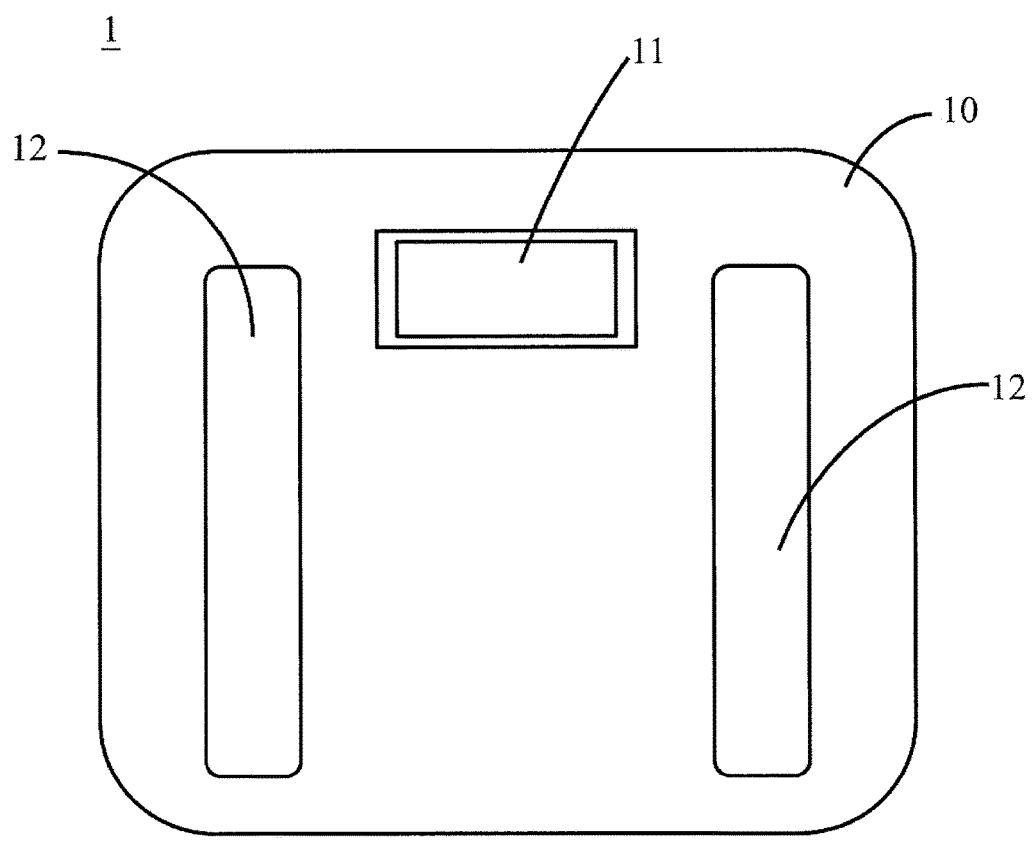
FIG. 1 is a schematic diagram illustrating a body fat measuring apparatus according to the present invention.
Figure 2:
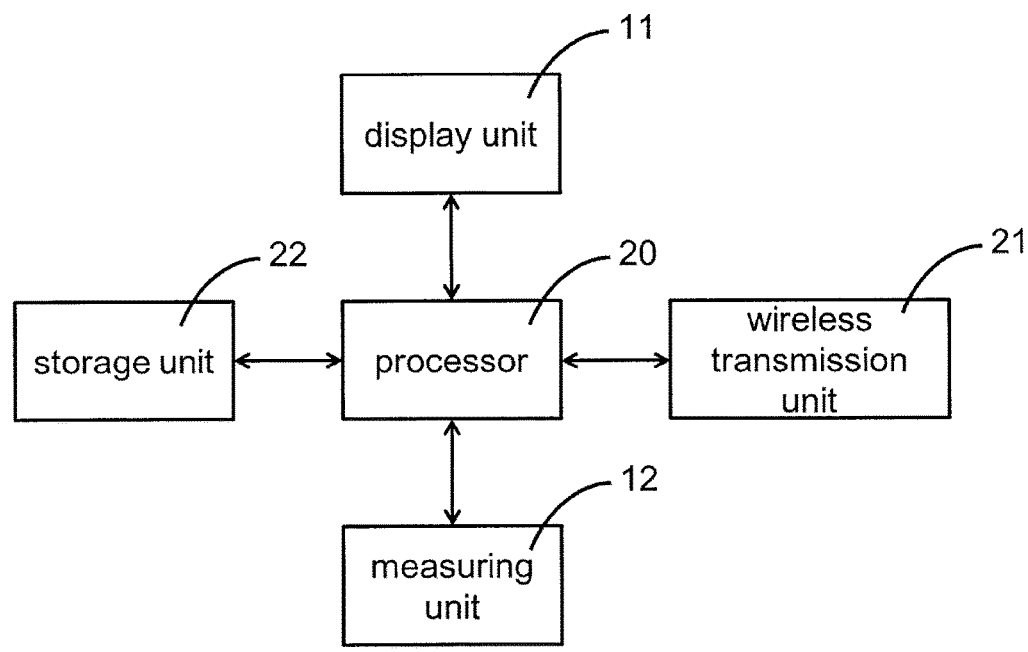
FIG. 2 is a schematic block diagram illustrating a body fat measuring apparatus according to the present invention.

The present invention provides a body fat measuring apparatus and the method thereof. Shown in FIG. 1 and FIG. 2, a body fat measuring apparatus 1 includes a case 10, a display unit 11, a measuring unit 12. The display unit 11 may be a liquid crystal display module with functional keys or a touching function. The measuring unit 12, which is a kind of measuring electrode, may determine a current body weight and a current impedance that are used as a current analysis data set. A processor 20 is included in the body fat measuring apparatus 1 and electrically coupled to the display unit 11, the measuring unit 12, a wireless transmission unit 21 and a storage unit 22. The storage unit 22 may cumulatively store one or more user names, user characteristic information related to the user names, recorded analysis data sets including recorded body weight and recorded impedance and the plurality of recorded analysis data sets corresponding to the user names.

Figure 3:
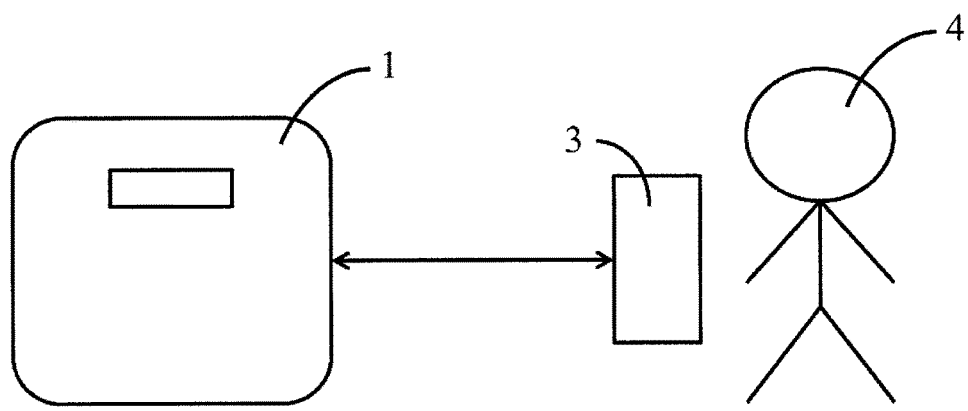
FIG. 3 is a schematic systematic diagram illustrating a body fat measuring apparatus and a portable electronic device according to the present invention.
Figure 4:
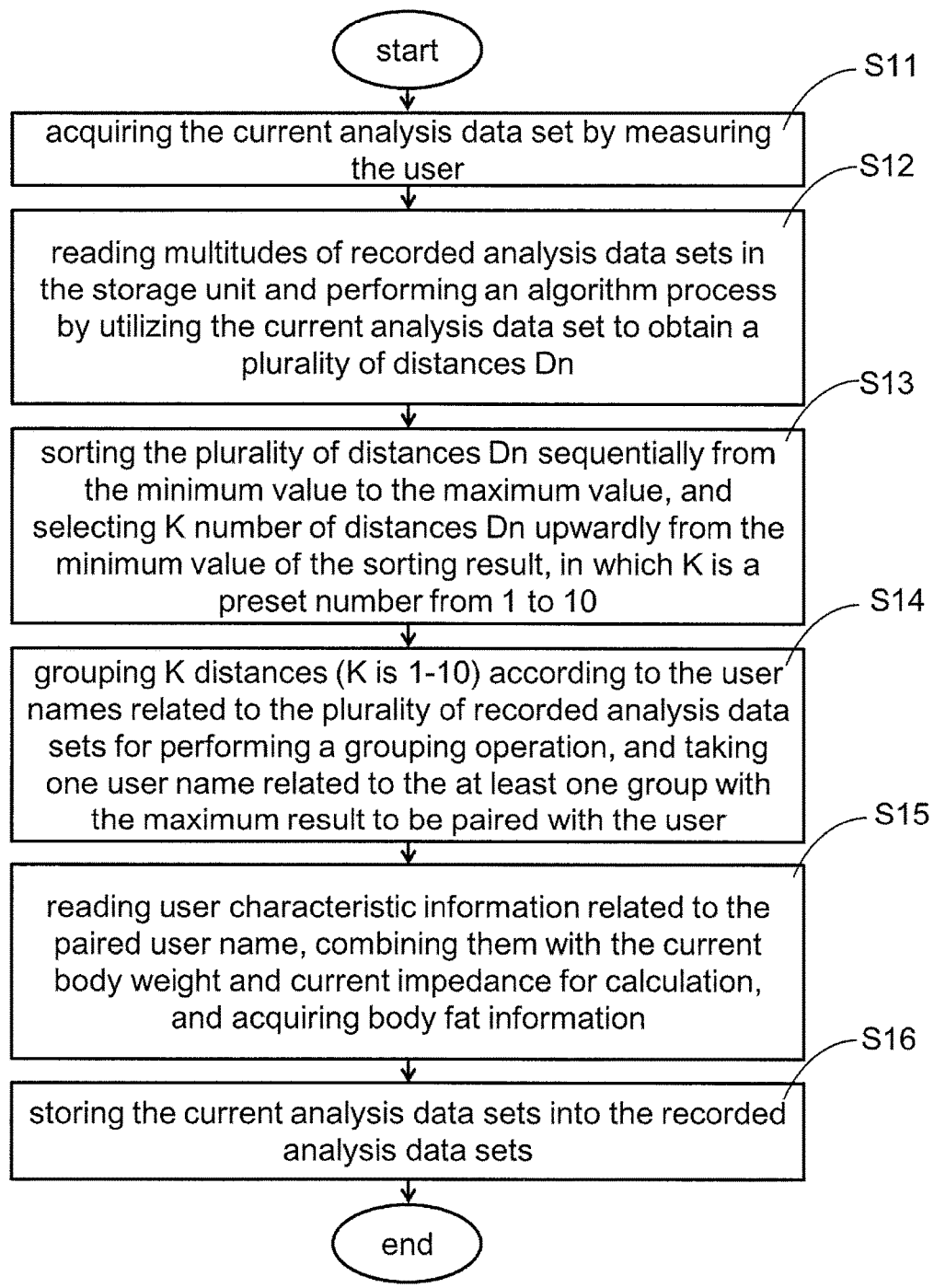
FIG. 4 is a schematic flow diagram illustrating a pairing method for a user and a user name according to the present invention.

Please refer to FIG. 3 and FIG. 4 which illustrate methods for pairing the user name and a user 4 and measuring body fat. Shown in FIG. 3, a portable electronic device 3 is coupled to the wireless transmission unit 21 via various wireless communications. The types of the wireless communication may be Wi-Fi, Bluetooth, Wi-Fi peaks (ZigBee), ultra-wideband (UWB), Sub-GHz, household high-frequency radio transmission (HomeRF), radio frequency identification (RFID) or near-field communication (NFC), and so on. The portable electronic device 3 may be a laptop with wireless communication, a tablet, a personal digital assistant, a mobile phone, a watch or a game console.

During measuring body fat, the user 4 may create a user name and user characteristic information related to the user name in the body fat measuring apparatus 1 via the portable electronic device 3 or by directly utilizing the display unit 11 with the touching function, and store the user name and the user characteristic information into the storage unit 22. The measuring unit 12 of the body fat measuring apparatus 1 measures the user to determine a current analysis data set of the user such as a current body weight and current impedance. In the meantime, body fat information of the user may be calculated out according to both parameters inputted by the user 4 in the user characteristic information such as height, gender and age and the parameters in the current analysis data set such as the current body weight and the current impedance.

In the case that the user inputs or recreates the user name and corresponding user characteristic information for the first time, the body fat measuring apparatus 1 calculates out fat information of the user 4 according to the current analysis data set of a current measurement and the user name and the corresponding user characteristic information that the user 4 inputs or recreates for the first time, instead of executing a step of pairing a user name with the user 4 during the current measurement. Then the current analysis data set of the current measurement is stored into the storage unit 22 to be used as a recorded analysis data set in a sample database, and each user name may have one or more corresponding recorded analysis data sets. Please refer to FIG. 4, in the case that the user measures his/her body fat with the body fat measuring apparatus 1 for the second time or other times, the measuring unit 12 of the body fat measuring apparatus 1 acquires the current analysis data set by measuring the user 4 (step S11). Next, a processor 20 reads multitudes of recorded analysis data sets in the storage unit 22 and performs an algorithm process by utilizing the current analysis data set to obtain a plurality of distances Dn (step S12). The algorithm process may be a KNN algorithm process that evaluates a possible class for an unknown class case by calculating a similarity degree with respect to a known class case.

$$Dn=|W-Wm|*\alpha+|Z-Zm|*\beta,$$

in which W represents the current body weight of the user 4 for the current time, Z represents the current impedance of the user 4 for the current time, Wm represents one of multitudes of recorded weights of the recorded analysis data sets in the storage unit 22, Zm represents one of multitudes of recorded impedances of the recorded analysis data sets in the storage unit 22, and β is the recorded analysis data sets correspond to their own user names, respectively. If the current body weight and the recorded body weight are take in kilogram, the range of α value is from 0.2~0.5. If the current body weight and the recorded body weight are take in gram, the range of α value is from 200~500. That is a value changes along with the changing of the unit of mass. In the case that the unit of mass is changed from kilogram into gram, the range of α value is scaled up 1000 times because the value of weight is scaled up 1000 times. Moreover, if the unit of impedance is ohm, the range of β value is from 1~5.

The core concept of KNN algorithm process is to find a user name that matches with the user 4 the most. The processor 20 performs KNN algorithm process by calculating the current body weight, the current impedance and the multitudes of recorded analysis data sets to obtain multitudes of distances Dn. Then the plurality of distances Dn are sorted sequentially from the minimum value to the maximum value to be selected K values out of distances Dn upwardly from the minimum value of the sorting result, in which K values is from 1 to 10 (step S13). The K (K is 1-10) values out of the plurality of distances are separately grouped according to the user names related to the plurality of recorded analysis data sets for performing a grouping operation, and one user name related to the at least one group with the maximum result is taken to be paired with the user (step S14). The grouping operation is a weighted distance operation that gets the reciprocals of K values out of the plurality of distances Dn and then adds these reciprocals. Next, the processor 20 reads the user characteristic information related to the paired user name, combines them with the current body weight and current impedance for calculation, and acquires body fat information (step S15). The body fat information includes BMI (body mass index), body fat percentage, body water content, bone mass, visceral fat content, basal metabolism, or body age. Next, the current analysis data sets are stored into the recorded analysis data sets (step S16).

For example, after the measurements of the current body weight and the current impedance of the user 4, in the case that the preset K equals to three in steps S12, S13, S14 and S15, the processor 20 obtains the multitudes of distances Dn from KNN algorithm process and sequentially sorts the multitudes of distances Dn from the minimum value to the maximum value. Three distances Dn are selected upwardly from the minimum value of the sorting result. When the three distances Dn respectively belong to two distances Da1 and Da2 of the user a and one distance Db1 of the user b, the distances Da1 and Da2 are grouped together and the distance Db1 is grouped separately. Next, the reciprocals of the distances Da1, Da2 and Db1 are summed for the weighted distance operation. One weighted distance for the user a represents La=(1/Da1)+(1/Da2), and the weighted distance for the user b represents Lb=1/Db1. Provided that the weighted distance La is more than the weighted distance Lb, the user name of the user a is paired with the user 4, and the user characteristic information related to the user a is read out. Reversely, the user name of the user b is paired with the user 4, and the user characteristic information related to the user b is read out.

Now, two men and two women who have different heights participate in measurement for accuracy comparison of a prior technology that identifies user with single recorded weight Wm and single recorded impedance Zm and the present invention that provides the algorithm process and grouping weighted distance operation for identification of user. Failure and success on user identification in different time are listed in Sheet 1.1 as follows:

Sheet 1.1

(P1, P2, P3, P4 represent ID of measured users; V represents success on identification; X represents failure on identification)

| | ID of | | Prior Art | | | | Algorithm Process of the Present Invention | | | |
|---|---|---|---|---|---|---|---|---|---|---|
| Sets | measured user | measurement time | weight | impedance | actual user | successful or not? | weight | impedance | actual user | successful or not? |
| 0 | P1 | 10:10 | 61.2 | 554 | Shown ID and | | 61.4 | 546 | Shown ID and | |
| | P2 | | 60.8 | 495 | data for each | | 61 | 481 | data for each | |
| | P3 | | 59.8 | 629 | user when a | | 59.8 | 632 | user when a | |
| | P4 | | 59.4 | 510 | recorded user | | 59.6 | 498 | recorded user | |

-continued

| Sets | ID of measured user | measurement time | Prior Art | | | | Algorithm Process of the Present Invention | | | |
|---|---|---|---|---|---|---|---|---|---|---|
| | | | weight | impedance | actual user | successful or not? | weight | impedance | actual user | successful or not? |
| | | | | | | name and a user are linked | | | | name and a user are linked |
| 1 | P1 | 11:37 | 61.9 | 542 | P1 | V | 62.2 | 523 | P1 | V |
| 2 | P3 | 11:42 | 59.6 | 632 | P3 | V | 59.7 | 624 | P3 | V |
| 3 | P2 | 11:44 | 60.8 | 493 | P2 | V | 61 | 480 | P2 | V |
| 4 | P4 | 11:53 | 59.4 | 503 | P4 | V | 59.6 | 460 | P4 | V |
| 5 | P1 | 13:38 | 61.6 | 517 | P1 | V | 61.8 | 509 | P1 | V |
| 6 | P2 | 13:41 | 61.3 | 479 | P1 | X | 61.5 | 465 | P2 | V |
| 7 | P3 | 13:44 | 60 | 624 | P3 | V | 60.1 | 616 | P3 | V |
| 8 | P4 | 13:46 | 59.9 | 498 | P3 | X | 59.9 | 441 | P4 | V |
| 9 | P2 | 15:09 | 61.5 | 494 | P1 | X | 61.6 | 474 | P2 | V |
| 10 | P3 | 15:12 | 60.2 | 608 | P2 | V | 60.4 | 608 | P3 | V |
| 11 | P1 | 15:14 | 61.7 | 534 | P1 | V | 61.9 | 500 | P1 | V |
| 12 | P4 | 15:19 | 59.9 | 474 | P3 | X | 60 | 469 | P4 | V |
| 13 | P1 | 17:12 | 61.3 | 513 | P1 | V | 61.6 | 494 | P1 | V |
| 14 | P2 | 17:13 | 61.5 | 489 | P1 | X | 61.6 | 477 | P2 | V |
| 15 | P3 | 17:15 | 60.2 | 611 | P2 | X | 60.4 | 604 | P3 | V |
| 16 | P4 | 17:18 | 60.1 | 473 | P2 | X | 60.2 | 465 | P4 | V |

Accordingly, in one prior known technology, there are identification mistakes in $6^{th}$, $8^{th}$, $9^{th}$, $12^{th}$, $14^{th}$, $15^{th}$ and $16^{th}$ sets. Oppositely, there is no identification mistake by using the algorithm process and grouping weighted distance operation of the present invention.

Not only are the current body weight and the current impedance of the present invention cumulatively stored into the storage 22 for long time recording and the sample database of the recorded analysis data set, but also are they together with body fat information transferred to a portable electronic device 3 for recording or reference by the user 4. Furthermore, once the user 4 finds any error identification happens, he or she can cut the link between the user name and the user 4 by using one functional key (not shown in figures) or touching function of the display unit 11 or the portable electronic device 3. The user 4 may rebuild one link between a new user name and the user characteristic information.

Accordingly, the present invention provides a body fat measuring apparatus, system and pairing method for user. It is convenient for user not to repeatedly input user name and user characteristic information. Furthermore, because the current body weight and the current impedance are used as user identification, accuracy of identification is far better than prior ones. Consequently, the body fat measuring apparatus of the present invention is a worthy task.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A body fat measuring apparatus, comprising:
   a measuring unit provided for determining a current body weight and a current impedance of a user, and the current body weight and the current impedance used as a current analysis data set;
   a portable electronic device or a display unit with a touching function provided for creating a user name and a user characteristic information related to the user name;
   a storage unit provided for cumulatively storing the user name, the user characteristic information related to the user name, and a plurality of recorded analysis data sets corresponding to the user names; and
   a processor provided for pairing the user name, reading the user characteristic information related to the user name from the storage unit, and obtaining a body fat information by calculating with the current body weight and the current impedance of the user;
   wherein the processor is further provided for:
      reading the current body weight, the current impedance and the plurality of recorded analysis data sets to perform an algorithm process to obtain a plurality of distances Dn, wherein the plurality of distances are obtained by calculating the current body weight, the current impedance and the plurality of recorded analysis data sets;
      sorting the plurality of distances Dn sequentially from the minimum value of the distance to the maximum value of the distance;
      selecting the K (K is 1-10) values out of the plurality of distances upwardly from the minimum value of the sorting result;
      grouping the K (K is 1-10) values out of the plurality of distances separately according to the user names related to the plurality of recorded analysis data sets to form at least one group;
      performing a grouping operation on each of the at least one group and taking the maximum result from the at least one group;
      pairing the user with the user name related to the at least one group with the maximum result; and
      storing the current analysis data set in the plurality of recorded analysis data sets of the storage unit corresponding the user names.

2. The body fat measuring apparatus according to claim 1, wherein the portable electronic device is a laptop, a tablet, a personal digital assistant, a mobile phone, a watch, or a game console.

3. The body fat measuring apparatus according to claim 1, further comprising a display unit, wherein a displaying information of the display unit includes the current body weight, the user name, and the user characteristic information that is related to the user name, or the body fat information.

4. The body fat measuring apparatus according to claim 1, wherein the body fat information includes BMI (body mass index), body fat percentage, body water content, bone mass, visceral fat content, basal metabolism, or body age.

5. The body fat measuring apparatus according to claim 1, wherein a calculation formula of the algorithm process is $$Dn=|W-Wm|*\alpha+|Z-Zm|*\beta,$$

wherein W is the current body weight, Z is the current impedance, Wm is one recorded body weight of the plurality of recorded analysis data sets, Zm is one recorded impedance of the plurality of recorded analysis data sets, and β is the recorded analysis data sets correspond to their own user names.

6. The body fat measuring apparatus according to claim 5, wherein when the units of the current body weight and the recorded body weight are kilograms, the range of α value is from 0.2~0.5, and when the units of the current impedance and the recorded impedance are ohms, the range of β value is from 1~5.

7. A body fat measuring system composed of a portable electronic device and a body fat measuring device, comprising: a wireless transmission unit, a measuring unit, a portable electronic device or a display unit with a touching function, a storage unit, and a processor, wherein the measuring unit determines a current body weight and a current impedance of a user as a current analysis data set; a portable electronic device or a display unit with a touching function is provided for creating a user name and a user characteristic information related to the user name; the storage unit stores a user name, a user characteristic information related to the user name, and a plurality of recorded analysis data sets corresponding to the user names cumulatively; the processor reads the current body weight, the current impedance and the plurality of recorded analysis data sets to perform an algorithm process to obtain a plurality of distances, then the plurality of distances are sorted sequentially from a minimum value to a maximum value; the processor selects the K (K is 1-10) values out of the plurality of distances upwardly from the minimum value of the sorting result and the K (K is 1-10) values out of the plurality of distances is then performed a grouping operation according to the user names related to the plurality of recorded analysis data sets, and the maximum result of the grouping operation is taken out, in which the user name of the maximum result is paired with the user, a body fat information is obtained by calculating with the current analysis data set and the user characteristic information related to the user name which is paired with the user, and then the current analysis data set is stored in the plurality of recorded analysis data sets of the storage unit corresponding to the user name; and the portable electronic device which is wirelessly connected with the wireless transmission unit, transfers the user name and the user characteristic information related to the user name to the body fat measuring device, or receives the body fat information via the wireless transmission unit.

8. The body fat measuring system according to claim 7, further comprising a display unit and a displaying information of the display unit including the current body weight, the user name, the user characteristic information related to the user name, or the body fat information.

9. The body fat measuring system according to claim 7, wherein the body fat information includes BMI (body mass index), body fat percentage, body water content, bone mass, visceral fat content, basal metabolism, or body age.

10. The body fat measuring system according to claim 7, wherein a calculation formula of the algorithm process is $$Dn=|W-Wm|*\alpha+|Z-Z|*\beta,$$

wherein W is the current body weight, Z is the current impedance, Wm is one recorded body weight of the plurality of recorded analysis data sets, Zm is one recorded impedance of the plurality of recorded analysis data sets, and β is the recorded analysis data sets correspond to their own user name.

11. The body fat measuring system according to claim 10, wherein when the units of the current body weight and the recorded body weight is kilograms, the range of α value is from 0.2~0.5, when the units of the current impedance and the recorded impedance is ohms, the range of β value is from 1~5.

12. The body fat measuring system according to claim 7, wherein the portable electronic device is a laptop, a tablet, a personal digital assistant, a mobile phone, a watch, or a game console.

13. The body fat measuring system according to claim 7, wherein the types of wireless communication comprise Wi-Fi, Bluetooth, Wi-Fi peaks, ultra-wideband, Sub-GHz, household high-frequency radio transmission, radio frequency identification, or short-range wireless communications.

* * * * *